US010794809B2

(12) United States Patent
Kawai et al.

(10) Patent No.: US 10,794,809 B2
(45) Date of Patent: Oct. 6, 2020

(54) METHOD FOR URINE SAMPLE ANALYSIS, REAGENT FOR URINE SAMPLE ANALYSIS, AND REAGENT KIT FOR URINE SAMPLE ANALYSIS (71) Applicant: SYSMEX CORPORATION, Kobe-shi, Hyogo (JP)

(72) Inventors: Akinori Kawai, Kobe (JP); Yuji Itose, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 58 days.

(21) Appl. No.: 15/121,411

(22) PCT Filed: Feb. 27, 2015

(86) PCT No.: PCT/JP2015/055883
§ 371 (c)(1),
(2) Date: Aug. 25, 2016

(87) PCT Pub. No.: WO2015/129863
PCT Pub. Date: Sep. 3, 2015

(65) Prior Publication Data
US 2016/0363521 A1 Dec. 15, 2016

(30) Foreign Application Priority Data
Feb. 28, 2014 (JP) ................. 2014-039282

(51) Int. Cl.
G01N 15/06 (2006.01)
G01N 1/30 (2006.01)
G01N 15/00 (2006.01)
G01N 15/14 (2006.01)
G01N 21/64 (2006.01)
G01N 33/493 (2006.01)
G01N 33/80 (2006.01)

(52) U.S. Cl.
CPC .............. G01N 15/06 (2013.01); G01N 1/30 (2013.01); G01N 21/6428 (2013.01); G01N 21/6458 (2013.01); G01N 33/493 (2013.01); G01N 33/80 (2013.01); G01N 15/1456 (2013.01); G01N 2015/0065 (2013.01); G01N 2015/0693 (2013.01); G01N 2021/6439 (2013.01); G01N 2201/0612 (2013.01)

(58) Field of Classification Search
None
See application file for complete search history.

(56) References Cited

U.S. PATENT DOCUMENTS

| 5,325,169 A | 6/1994 | Nakamoto et al. |
| 5,496,734 A | 3/1996 | Sakata |
| 5,516,700 A * | 5/1996 | Smith .................. C12Q 1/26 436/164 |
| 5,693,484 A | 12/1997 | Nakamoto et al. |
| 5,728,582 A | 3/1998 | Taki et al. |
| 5,891,733 A | 4/1999 | Inoue |
| 2002/0076743 A1* | 6/2002 | Sakai ....................... C12Q 1/04 435/34 |
| 2003/0215890 A1* | 11/2003 | Ornstein .................. A01N 1/00 435/7.2 |
| 2003/0219850 A1 | 11/2003 | Tsuji et al. |
| 2006/0073601 A1* | 4/2006 | Kawashima ..... C01N 33/56961 436/63 |
| 2006/0073606 A1 | 4/2006 | Fukuda |
| 2007/0013906 A1 | 1/2007 | Kawate |
| 2007/0177146 A1* | 8/2007 | Fujimoto ........... G01N 15/1404 356/338 |
| 2007/0269897 A1 | 11/2007 | Tanaka et al. |
| 2009/0050821 A1* | 2/2009 | Tanaka ............... G01N 15/1459 250/458.1 |
| 2009/0206234 A1* | 8/2009 | Okuda ...................... G01J 3/46 250/201.2 |

FOREIGN PATENT DOCUMENTS

| CN | 1092172 A | 9/1994 |
| CN | 1880942 A | 12/2006 |
| CN | 106062556 A | 10/2016 |
| EP | 0695936 A2 | 2/1993 |
| EP | 0545313 A1 | 6/1993 |
| EP | 0708334 A2 | 4/1996 |
| EP | 0708334 A3 | 9/1996 |
| EP | 0695936 A3 | 8/1997 |
| EP | 1837402 A1 | 9/2007 |
| EP | 1857804 A2 | 11/2007 |
| EP | 1865318 A1 | 12/2007 |
| EP | 1857804 A3 | 7/2008 |
| EP | 2963418 A1 | 1/2016 |
| EP | 3112862 A1 | 1/2017 |
| JP | 4-278460 A | 10/1992 |

(Continued)

OTHER PUBLICATIONS

Ringsrud, K.M. 2001. Casts in the urine sediment. Laboratory Medicine 32(4): 191-193. specif. p. 191.*
Hyodo, T. et al. 1997. Analysis of urinary red blood cells of healthy individuals by an automated urinary flow cytometer. Nephron 75(4): 451-457. specif. pp. 451, 453, 454.*
International Search Report for PCT/JP2015/055883 dated May 26, 2015 [PCT/ISA/210].
Supplementary European Search Report; 15754422.2-1405/ 3112862 for PCT/JP2015055897; with Information on Search Strategy EP 15 75 5480; dated Aug. 25, 2017.
Communication dated Jan. 16, 2020 from the Intellectual Property India Patent Office in application No. 201637032085.
The Brazilian Office Action dated Oct. 8, 2019 in a counterpart Brazilian patent application No. BR112016019721-6.

(Continued)

Primary Examiner — Renee Claytor
Assistant Examiner — Sharon M. Papciak
(74) Attorney, Agent, or Firm — Sughrue Mion, PLLC (57) ABSTRACT The present invention relates to a method for analyzing urine sample, a reagent for the analysis of a urine sample and a reagent kit for the analysis of a urine sample, which are used for detecting at least casts and erythrocytes as urinary particles.

19 Claims, 5 Drawing Sheets (56) References Cited

FOREIGN PATENT DOCUMENTS

| | | | |
|---|---|---|---|
| JP | 4-337459 | A | 11/1992 |
| JP | H04337459 | A | 11/1992 |
| JP | 5-322883 | A | 12/1993 |
| JP | 06207942 | A | 7/1994 |
| JP | 8-5543 | A | 1/1996 |
| JP | H08170960 | A | 7/1996 |
| JP | 9-329596 | A | 12/1997 |
| JP | 2002090365 | A | 3/2002 |
| JP | 2006-98233 | A | 4/2006 |
| JP | 2006-105625 | A | 4/2006 |
| JP | 2007047154 | A | 2/2007 |
| JP | 2007-309765 | A | 11/2007 |
| WO | 2015129869 | A1 | 9/2015 |

\* cited by examiner

METHOD FOR URINE SAMPLE ANALYSIS, REAGENT FOR URINE SAMPLE ANALYSIS, AND REAGENT KIT FOR URINE SAMPLE ANALYSIS

CROSS REFERENCE TO RELATED APPLICATIONS

This application is a National Stage of International Application No. PCT/JP2015/055883, filed on Feb. 27, 2015, which claims priority from Japanese Patent Application No. 2014-039282, filed on Feb. 28, 2014, the contents of all of which are incorporated herein by reference in their entirety.

TECHNICAL FIELD

The present invention relates to a method for analyzing urine sample, a reagent for analysis of urine sample and a reagent kit for analysis of urine sample, which are for detecting at least casts and erythrocytes as urinary particles.

BACKGROUND ART

In diseases such as infectious diseases, inflammatory lesions, degenerative lesions, calculus diseases, tumors and the like in nephric and urinary systems, a variety of particles appear in the urine depending on the individual diseases. The particles may include erythrocytes, casts, leukocytes, epithelial cells, yeast like fungi, spermatozoa and the like. Analysis of these particles in the urine is important for estimating the disease and the abnormal site in nephric and urinary systems. For example, erythrocytes are useful urinary particles for determining the presence or absence of bleeding in the route from the glomerulus of the kidney to the urethra.

A cast is a solid particle having a coagulation precipitate composed of Tamm-Horsfall mucoprotein and urinary plasma protein (principally albumin) as a basic component. The cast is formed principally in the distal renal tubule and the collecting tubule. While the cast composed exclusively of the basic component is called a hyaline cast, various components such as cells may be enclosed in the hyaline cast depending on the condition of the kidney or the renal tubule, with the result that a further degenerated cast could be formed. Therefore, the casts are useful urinary particles for grasping the disease condition and the degree of the disorder of the kidney and the renal tubule.

In analysis of the urinary particles such as casts and erythrocytes, a visual inspection is widely conducted by observing the precipitate (particles) obtained by centrifugal separation of the urine under a microscope. In recent years, an automated analysis method using a flow cytometer has been developed. For example, Patent Document 1 discloses a method for analyzing the urinary particles by measuring a urine sample treated with a staining reagent and a diluting reagent by a flow cytometer.

Meanwhile, the urine also contains the particles which extremely resemble the casts in shape, such as mucus threads and aggregates of bacteria or salts. Since the number of casts in a urine sample is the clinically important information, it is important for the detection of the casts to discriminate the casts from the particles which resemble the casts, such as mucus threads.

CITATION LIST

Patent Document

Patent Document 1: Japanese Unexamined Patent Publication No. HEI 9(1997)-329596

SUMMARY OF THE INVENTION

Problems to be Solved by the Invention

Patent Document 1 discloses that leukocytes are discriminated from small epithelial cells by adding a surfactant as a cell membrane damaging agent to a urine sample in a concentration of about 50 to 5000 mg/L to damage and strongly stain the leukocytes. Further, Patent Document 1 discloses that erythrocytes can be discriminated from crystal components and yeast like fungi by comparing the measurement result of the sample in which erythrocytes are hemolyzed by a cell membrane damaging agent, with the measurement result of the sample in which erythrocytes are not hemolyzed.

However, it is complicated to prepare two samples and analyze each of the samples for analyzing the erythrocytes in the urine. It is thus desired that the urinary erythrocytes can be detected from one urine sample. As described above, discrimination of casts from mucus threads is important to detect the urinary casts. Therefore, in order to accurately detect the urinary casts and the erythrocytes from one urine sample, there is a demand for detecting the erythrocytes without causing hemolysis and for allowing detection of the casts discriminably from the impurities such as mucus threads.

In light of the above, an object of the present invention is to provide a method for analyzing urine sample that allows accurate detection of casts and erythrocytes from one urine sample. Further, an object of the present invention is to provide a reagent and a reagent kit for analysis of urine sample that are suitably used for the method.

Solution to the Problems

The present inventors surprisingly have found that by extremely decreasing the concentration of the surfactant in the measurement sample to the level of more than or equal to 2 mg/L and less than or equal to 30 mg/L, erythrocytes can be detected without substantially damaging them, and casts can be detected discriminably from the impurities, thereby achieving the present invention.

Therefore, the present invention provides a method for analyzing a urine sample, comprising the steps of preparing a measurement sample by mixing the urine sample and a reagent containing a surfactant, and detecting at least casts and erythrocytes as urinary particles contained in the measurement sample obtained from the preparation step, wherein a concentration of the surfactant in the measurement sample obtained from the preparation step is more than or equal to 2 mg/L and less than or equal to 30 mg/L.

The present invention also provides a reagent for analysis of urine sample for detecting at least casts and erythrocytes as urinary particles, containing more than or equal to 4 mg/L and less than or equal to 50 mg/L of a surfactant.

Further, the present invention provides a reagent kit for analysis of urine sample for detecting at least casts and erythrocytes as urinary particles, comprising a first reagent containing more than or equal to 4 mg/L and less than or equal to 50 mg/L of a surfactant, and a second reagent containing a fluorescent dye for staining casts and erythrocytes.

Effects of the Invention

The present invention allows accurate detection of casts and erythrocytes without substantially damaging the erythrocytes.

EMBODIMENTS OF THE INVENTION

[Method for Analyzing Urine Sample]

A method for analyzing a urine sample (hereinafter, also simply referred to as "method") of the present embodiment is intended to analyze erythrocytes, casts, crystal components and mucus threads among urinary particles, and is particularly preferred for analyzing casts and erythrocytes.

Various kinds of casts are known, for example, hyaline casts that are composed exclusively of the above-described basic component, epithelial casts in which renal tubular epithelial cells are enclosed, red blood cell casts in which erythrocytes are enclosed, white blood cell casts in which leukocytes are enclosed, fatty casts in which fatty granules are enclosed, granular casts in which granular components (principally the degenerated epithelial cells) are enclosed, and waxy casts in which the entire or part of the casts are uniform and degenerated as a wax. In the present embodiment, the kind of casts is not particularly limited.

In the present embodiment, the kind of erythrocytes is not particularly limited, and may include any of normal erythrocytes and abnormal erythrocytes.

In the method of the present embodiment, first, a step of preparing a measurement sample by mixing a urine sample and a reagent containing a surfactant (hereinafter, also referred to as "first reagent") is conducted. In this step, the urine sample and the first reagent are mixed so that the concentration (final concentration) of the surfactant in the obtained measurement sample is more than or equal to 2 mg/L and less than or equal to 30 mg/L. Preferably, they are mixed so that the concentration of the surfactant in the measurement sample is more than or equal to 4 mg/L and less than or equal to 22 mg/L.

In the present embodiment, the urine sample is not particularly limited as far as it is a liquid sample containing the urinary particles, and is preferably the urine collected from a subject. In the case of using the urine collected from the subject as a sample, it is desired to use the urine sample for the method of the present embodiment within 24 hours, particularly within 3 to 12 hours after collection because the urinary particles may be deteriorated with time.

In the method of the present embodiment, although the concentration of the surfactant in the measurement sample is markedly lowered to the level of more than or equal to 2 mg/L and less than or equal to 30 mg/L, the aggregates of the impurities such as bacteria or salts that inhibit accurate detection of casts can be dispersed and removed by the action of the surfactant.

The first reagent can be obtained by dissolving the surfactant in an appropriate solvent. The solvent is not particularly limited as far as it can dissolve the surfactant and may include, for example, water, a water-soluble organic solvent and a mixture thereof. Examples of the water-soluble organic solvent include lower alcohols having 1 to 3 carbon atoms, ethylene glycol and dimethylsulfoxide (DMSO). In the present embodiment, water is particularly preferred.

The kind of the surfactant used in the first reagent is not particularly limited and can be appropriately selected from cationic surfactants, nonionic surfactants, anionic surfactants and amphoteric surfactants. The surfactant used in the first reagent is preferably selected from cationic surfactants and nonionic surfactants, and cationic surfactants are particularly preferred. The first reagent may contain one surfactant or two or more surfactants. When two or more surfactants are contained, the combination thereof may be optionally selected.

In the present embodiment, as the cationic surfactant, at least one selected from quaternary ammonium salt type surfactants and pyridinium salt type surfactants may be used. The quaternary ammonium salt type surfactant may include, for example, the surfactants having 4 to 38 carbon atoms in total represented by the following formula (I).

[Chemical formula 1]

In the above formula (I), $R_1$ is an alkyl or alkenyl group having 1 to 18 carbon atoms; $R_2$ and $R_3$ are the same or different from each other and are respectively an alkyl or alkenyl group having 1 to 4 carbon atoms; $R_4$ is an alkyl or alkenyl group having 1 to 12 carbon atoms, or a benzyl group; and $X^-$ is a halogen ion or a hydroxyl ion.

In the above formula (I), $R_1$ is preferably an alkyl group or an alkenyl group having 6, 8, 10, 12 or 14 carbon atoms and is particularly preferably a linear alkyl group. More specifically, $R_1$ may include an octyl group, a decyl group and a dodecyl group. $R_2$ and $R_3$ are preferably a methyl group, an ethyl group and a propyl group. $R_4$ is preferably a methyl group, an ethyl group and a propyl group. More preferably, each of $R_2$, $R_3$ and $R_4$ is a methyl group. In the above formula (I), $X^-$ is preferably a halogen ion and include, for example, a bromide ion, a chloride ion and an iodide ion.

The pyridinium salt type surfactant may include, for example, the surfactants represented by the following formula (II).

[Chemical formula 2]

(II)

In the above formula (II), $R_1$ is an alkyl or alkenyl group having 6 to 18 carbon atoms; and $X^-$ is a halogen ion.

In the above formula (II), $R_1$ is preferably an alkyl or alkenyl group having 6, 8, 10, 12 or 14 carbon atom and is particularly preferably a linear alkyl group. More specifically, $R_1$ include an octyl group, a decyl group and a dodecyl group.

Specific examples of the cationic surfactant include triethylmethylammonium chloride, didecyldimethylammonium bromide, didecyldimethylammonium chloride, didodecyldimethylammonium bromide, didodecyldimethylammonium chloride, ethylhexadecyldimethylammonium bromide, ethyltrimethylammonium iodide, dodecyltrimethylammonium bromide, decyltrimethylammonium bromide, dodecyltrimethylammonium chloride, octyltrimethylammonium bromide, octyltrimethylammonium chloride, tetradecyltrimethylammonium chloride, trimethylheptadecylammonium bromide, hexadecyltrimethylammonium bromide, hexadecyltrimethylammonium chloride, hexadecyltrimethylammonium hydroxide, hexyltrimethylammonium bromide, trimethylnonylammonium bromide, trimethylstearylammonium bromide, trimethylstearylammonium chloride, dodecylpyridinium chloride and tetradecyltrimethylammonium bromide. Among these, dodecyltrimethylammonium bromide (DTAB), dodecyltrimethylammonium chloride (DTAC), octyltrimethylammonium bromide (OTAB) and tetradecyltrimethylammonium bromide (MTAB) are preferable, and DTAB is particularly preferable.

In the present embodiment, as the nonionic surfactant, the polyoxyethylene-based nonionic surfactants represented by the following formula (III) are preferably used.

(III)

In the above formula (III), $R_1$ is an alkyl, alkenyl or alkynyl group having 8 to 25 carbon atoms; $R_2$ is —O—, —COO— or

[Chemical formula 3]

;

and n is an integer of 10 to 50.

Specific examples of the nonionic surfactant include polyoxyethylene alkyl ether, polyoxyethylene sterol, polyoxyethylene castor oil, polyoxyethylene sorbit fatty acid ester, polyoxyethylene alkyl amine, polyoxyethylene polyoxypropylene alkyl ether and the like. Among these, polyoxyethylene alkyl ether is preferable, and more specifically, polyoxyethylene lauryl ether, polyoxyethylene cetyl ether, polyoxyethylene stearyl ether, polyoxyethylene oleyl ether and polyoxyethylene behenyl ether are particularly preferable.

In the present embodiment, as the anionic surfactant, at least one kind selected from the carboxylate type surfactants, the sulfonate type surfactants and the sulfuric acid ester salt type surfactants may be used. The carboxylate type surfactant includes, for example, the surfactants represented by the following formula (IV).

(IV)

In the above formula (IV), $R_1$ is an alkyl, alkenyl or alkynyl group having 8 to 25 carbon atoms; and $Y^+$ is an alkali metal ion.

In the above formula (IV), $R_1$ is preferably a linear alkyl group having 12 to 18 carbon atoms. The carboxylate type surfactants are known as soap in the art and examples thereof include sodium laurate, sodium stearate, sodium oleate and the like.

The sulfonate type surfactant may include, for example, the surfactants represented by the following formula (V).

[Chemical formula 4]

(V)

In the above formula (V), m and n are an integer of 0 or more, the sum of m and n is 8 to 25; and $Y^+$ is an alkali metal ion.

Preferably, the sum of m and n in the formula (V) is 9 to 18. The sulfonate type surfactants represented by the above formula (V) are known as alkyl benzene sulfonates in the art and examples thereof include sodium linear decylbenzene sulfate, sodium linear undecylbenzene sulfate, sodium linear dodecylbenzene sulfate, sodium linear tridecylbenzene sulfate, sodium linear tetradecylbenzene sulfate and the like.

Also, as the sulfonate type surfactant, a mixture of surfactants respectively represented by the following formulas (VI) and (VII) may be used.

(VI)

In the above formula (VI), j and k are an integer of 0 or more, the sum of j and k is an integer of 10 to 25; and $Y^+$ is an alkali metal ion.

(VII)

In the above formula (VII), m and n are an integer of 0 or more, the sum of m and n is an integer of 10 to 25; and $Y^+$ is an alkali metal ion.

Preferably, the sum of j and k in the above formula (VI) is an integer of 11 to 15, and the sum of m and n in the above formula (VII) is an integer of 12 to 16. The surfactants respectively represented by the above formulas (VI) and (VII) are also known as α-olefin sulfonates in the art and examples thereof include sodium 1-tetradecene sulfonate, sodium hexadecene sulfonate, sodium 3-hydroxyhexadecyl-1-sulfonate, sodium octadecene-1-sulfonate, sodium 3-hydroxy-1-octadecane sulfonate and the like.

The sulfuric acid ester salt type surfactant may include, for example, the surfactants represented by the following formula (VIII).

$$R_1—O—SO_3^-Y^+ \quad \text{(VIII)}$$

In the above formula (VIII), $R_1$ represents an alkyl, alkenyl or alkynyl group having 10 to 25 carbon atoms; and $Y^+$ represents an alkali metal ion.

In the above formula (VIII), $R_1$ is preferably a linear alkyl group having 10 to 18 carbon atoms, and is particularly preferably a linear alkyl group having 12 carbon atoms. The sulfuric acid ester salt type surfactants represented by the above formula (VIII) are known as higher alcohol sulfate salt in the art and examples thereof include sodium decyl sulfate, sodium undecyl sulfate, sodium dodecyl sulfate, sodium tridecyl sulfate, sodium tetradecyl sulfate and the like.

Also, as the sulfuric acid ester salt type surfactant, the surfactants represented by the following formula (IX) may be used.

$$R_1—O—(CH_2CH_2O)_n—SO_3^-Y^+ \quad \text{(IX)}$$

In the above formula (IX), $R_1$ is an alkyl, alkenyl or alkynyl group having 10 to 25 carbon atoms; n is an integer of 1 to 8; and $Y^+$ is an alkali metal ion or an ammonium ion.

In the above formula (IX), $R_1$ is preferably a linear alkyl having 12 to 18 carbon atoms, and is particularly preferably a linear alkyl group having 12 carbon atoms. The sulfuric acid ester salt type surfactants represented by the above formula (IX) are known as polyoxyethylene alkyl sulfuric acid ester salt in the art and examples thereof include sodium dodecyl ether sulfuric acid ester and the like.

As the sulfuric acid ester salt type surfactant, a surfactant represented by the following formula (X) may be used.

$$R_1—CH(—SO_3^-)—COOCH_3Y^+ \quad \text{(X)}$$

In the above formula (X), $R_1$ is an alkyl, alkenyl or alkynyl group having 8 to 25 carbon atoms; and $Y^+$ is an alkali metal ion.

In the above formula (X), $R_1$ is preferably a linear alkyl group having 10 to 18 carbon atoms, and is particularly preferably a linear alkyl group having 12 carbon atoms. The sulfuric acid ester salt type surfactants represented by the above formula (X) are known as α-sulfo fatty acid esters in the art and examples thereof include 2-sulfotetradecanoic acid-1-methylester sodium salt, 2-sulfohexadecanoic acid-1-methylester sodium salt and the like.

In the present embodiment, as the amphoteric surfactant, at least one kind selected from amino acid type amphoteric surfactants and betaine type amphoteric surfactants may be used. The amino acid type amphoteric surfactant may include, for example, the surfactants represented by the following formula (XI).

$$R_1—N^+H_2—CH_2CH_2COO^- \quad \text{(XI)}$$

In the above formula (XI), $R_1$ is an alkyl, alkenyl or alkynyl group having 8 to 25 carbon atoms.

In the above formula (XI), $R_1$ is preferably a linear alkyl group having 12 to 18 carbon atoms. The above amino acid type amphoteric surfactant may include, for example, 3-(dodecylamino)propanoic acid, 3-(tetradeca-1-ylamino)propanoic acid and the like.

The betaine type amphoteric surfactant include, for example, the surfactants represented by the following formula (XII).

[Chemical formula 5]

$$\begin{array}{c} R_1 \\ | \\ R_2—N^+—(CH_2)_nCOO^- \\ | \\ R_3 \end{array} \quad \text{(XII)}$$

In the above formula (XII), $R_1$ is an alkyl or alkenyl group having 6 to 18 carbon atoms; $R_2$ is an alkyl or alkenyl group having 1 to 4 carbon atoms; $R_3$ is an alkyl or alkenyl group having 1 to 4 carbon atoms, or a benzyl group; and n is 1 or 2.

The betaine type amphoteric surfactant may include, for example, dodecyldimethylaminoacetic acid betaine, stearyldimethylaminoacetic acid betaine and the like.

The concentration of the surfactant in the first reagent is not particularly limited as far as it can provide the concentration of the surfactant in the prepared measurement sample of more than or equal to 2 mg/L and less than or equal to 30 mg/L, preferably more than or equal to 4 mg/L and less than or equal to 22 mg/L.

In the present embodiment, in order to prevent hemolysis of erythrocytes due to change in pH, pH of the first reagent can be adjusted in the range of higher than or equal to 5 and lower than or equal to 9, preferably in a range of higher than or equal to 6.5 and lower than or equal to 8.6, and more preferably in a range of higher than or equal to 7.0 and lower than or equal to 7.8. Therefore, in order to keep pH constant, the first reagent may contain a buffer. The buffer is not particularly limited as far as it has the buffering action in the aforementioned pH ranges and examples thereof include Good's buffers such as Tris, MES, Bis-Tris, ADA, PIPES, ACES, MOPS, MOPSO, BES, TES, HEPES, DIPSO, TAPSO, POPSO, HEPPSO, EPPS, Tricine, Bicine, TAPS and the like.

Some urine samples contain amorphous salts such as ammonium phosphate, magnesium phosphate and calcium carbonate. In the present embodiment, the first reagent may contain a chelating agent for reducing the influence of these amorphous salts. The chelating agent is not particularly limited as far as it is a chelating agent capable of removing amorphous salts, and can be appropriately selected from calcium removing agents and magnesium removing agents that are known in the art. Specific examples include ethylenediaminetetraacetate (EDTA salt), CyDTA, DHEG, DPTA-OH, EDDA, EDDP, GEDTA, HDTA, HIDA, Methyl-EDTA, NTA, NTP, NTPO, EDDPO and the like, and among these, EDTA salt is particularly preferable.

The concentration of the chelating agent in the first reagent is desirably set so that the chelating agent is contained in such a final concentration that can reduce the influence of the amorphous salts in the measurement sample prepared in the manner as described above. The final concentration in the measurement sample may be appropriately set depending on the kind of the chelating agent. For example, when EDTA 2 potassium (EDTA-2K) is used as the chelating agent, the final concentration in the measurement sample is more than or equal to 0.1 mM and less than or equal to 500 mM, preferably more than or equal to 1 mM and less than or equal to 100 mM.

It is known that in the case where yeast like fungi and erythrocytes are present in the urine, fractionation between the yeast like fungi and the erythrocytes is sometimes not good in the analysis by a flow cytometer. Therefore, the first reagent may contain a substance that damages cell membranes of yeast like fungi. Examples of such a substance include 2-phenoxy ethanol, benzyl alcohol, phenethyl alcohol, 1-phenoxy-2-propanol, phenol, phenyl acetate, benzothiazole and the like, and among these, 2-phenoxy ethanol is particularly preferable. By using the first reagent containing such a substance, the stainability of the yeast like fungi changes, and fractionation between the erythrocytes and the yeast like fungi is improved.

The osmotic pressure of urine is known to distribute in a wide range of 50 to 1300 mOsm/kg. When the osmotic pressure is too low or too high in the measurement sample, there is a fear that erythrocytes are damaged. An appropriate osmotic pressure in the measurement sample is more than or equal to 100 mOsm/kg and less than or equal to 600 mOsm/kg, preferably more than or equal to 150 mOsm/kg and less than or equal to 500 mOsm/kg. When the osmotic pressure of the urine is too high, the osmotic pressure can be appropriately adjusted by diluting the urine with water or the first reagent. On the other hand, when the osmotic pressure of the urine is too low, the first reagent may contain an osmotic pressure compensating agent. The osmotic pressure compensating agent may include inorganic salts, organic salts, saccharides and the like. Examples of the inorganic salts include sodium chloride, sodium bromide and the like. Examples of the organic salts include sodium propionate, potassium propionate, ammonium propionate oxalate and the like. Examples of the saccharides include sorbitol, glucose, mannitol and the like.

In the present embodiment, it is preferred to further mix a reagent containing a fluorescent dye for staining casts and erythrocytes (hereinafter, also referred to as "second reagent") in the preparation step. The fluorescent dye contained in the second reagent is preferably a fluorescent dye capable of staining at least cell membranes, preferably cell membranes of erythrocytes and protein. Examples of the fluorescent dye that can be used in the second reagent include condensed benzene derivatives, and among the derivatives, a cyanine-based fluorescent dye is particularly preferable. Examples of the cyanine-based fluorescent dye include 3,3'-diethyloxacarbocyanine iodide (DiOC2 (3)), 3,3-dipropyloxacarbocyanine iodide (DiOC3(3)), 3,3'-dibutyloxacyanine iodide (DiOC4(3)) and 3,3-dipentyloxacarbocyanine iodide (DiOC5(3)).

The second reagent may contain one fluorescent dye or two or more fluorescent dyes. The concentration of the fluorescent dye in the second reagent is desirably set so that the fluorescent dye is contained in such a final concentration capable of appropriately staining at least casts and erythrocytes in the prepared measurement sample. The final concentration in the measurement sample may be appropriately set depending on the kind of the fluorescent dye. For example, when DiOC3(3) is used as the fluorescent dye, the final concentration in the measurement sample is more than or equal to 0.1 µg/mL and less than or equal to 200 µg/mL, preferably more than or equal to 1 µg/mL and less than or equal to 20 µg/mL.

The second reagent can be obtained by dissolving the fluorescent dye in an appropriate solvent. The solvent is not particularly limited as far as it is an aqueous solvent capable of dissolving the fluorescent dye and examples thereof include water, a water-soluble organic solvent and a mixture thereof. Among these, a water-soluble organic solvent is particularly preferable. Examples of the water-soluble organic solvent include lower alcohols having 1 to 3 carbon atoms, ethylene glycol, DMSO and the like.

In the present embodiment, the urine sample, the first reagent, and the second reagent may be mixed in any order without limitation, and these may be mixed at the same time. Preferably, the urine sample and the second reagent are mixed previously, and then the first reagent is further mixed therein. Alternatively, the first reagent and the second reagent may be mixed previously, and then the urine sample may be further mixed therein.

In the present embodiment, the mixing ratio of the urine sample, the first reagent, and the second reagent is not particularly limited, and may be appropriately determined depending on the component concentrations contained in the respective reagents. For example, the mixing ratio between the urine sample and the first reagent can be determined within the range of 1:0.5 to 10 by volume ratio. The mixing ratio between the urine sample and the second reagent can be determined within the range of 1:0.01 to 1 by volume ratio. The amount of the urine sample can be appropriately determined depending on the first reagent and the second reagent. The amount of the urine sample is preferably less than or equal to 1000 µL so that the measurement time is not too long. A sufficient amount of the urine sample used for the measurement is about 10 to 1000 µL.

The temperature condition in the preparation step is 10 to 60° C., preferably 35 to 45° C. Each reagent may be previously heated to the above temperature. After mixing the urine sample, the first reagent and/or the second reagent, the mixture may be incubated for 1 second to 5 minutes, preferably 5 to 60 seconds.

In the method of the present embodiment, the step of detecting at least casts and erythrocytes as urinary particles contained in the measurement sample obtained in the above preparation step is conducted.

In the case where the second reagent is not used in the preparation step, particles including casts and erythrocytes can be detected by observing the shapes and the internal structures of the respective particles in the measurement sample under an optical microscope. In the case where particles in the urine sample are stained with the second reagent, particles can be detected by observing the shapes and the degrees of staining of the particles in the measurement sample under a fluorescence microscope.

In a preferred embodiment, prior to the detection step, a step of obtaining optical information by irradiating urinary particles contained in the measurement sample with light is further conducted. The optical information obtention step is desirably conducted by a flow cytometer. In the measurement by a flow cytometer, by irradiating stained urinary particles with light when the particles pass through a flow cell, the optical information can be obtained as signals emitted from the particles. Preferably, the obtained optical information contains at least scattered light information. In the case where the measurement sample is prepared by using the second reagent, it is preferred to obtain scattered light information and fluorescence information as the optical information.

The scattered light information is not particularly limited as far as it is the information of scattered light that can be measured on a conventional commercially available flow cytometer. The scattered light information may include, for example, intensity and waveform information of scattered light such as forward scattered light (e.g. light receiving angle of about 0 to 20 degrees) and side scattered light (light receiving angle of about 90 degrees). More specifically, the scattered light information includes an intensity of scattered light, a pulse width of scattered light, an integral value of scattered light and the like. It is known in the art that side scattered light reflects the internal information of cells such as nuclei and granules, and forward scattered light reflects the information of the size of cells. In the embodiment, it is preferred to use the information of forward scattered light.

The fluorescence information is not particularly limited as far as it is the information obtained by irradiating the stained urinary particles with excitation light having an appropriate wavelength and measuring the excited fluorescence. The fluorescence information may include, for example, an intensity and a waveform of fluorescence. More specifically, the fluorescence information includes an intensity of fluorescence, a pulse width of fluorescence, an integral value of fluorescence and the like. The fluorescence is emitted from nucleic acid or the like in the particles stained by the fluorescent dye contained in the second reagent. The receiving wavelength can be appropriately selected depending on the fluorescent dye contained in the second reagent.

In the present embodiment, the light source of the flow cytometer is not particularly limited, and a light source having a suitable wavelength for excitation of the fluorescent dye can be appropriately selected. For example, a red semiconductor laser, a blue semiconductor laser, an argon laser, a He—Ne laser, a mercury arc lamp or the like may be used. In particular, a semiconductor laser is suitable because it is very low in price compared with a gas laser.

In the method of the present embodiment, when the aforementioned obtention step is conducted, at least casts and erythrocytes are detected as urinary particles in the detection step, based on the optical information obtained in the obtention step. The term "detection" embraces not only finding the existence of the urinary particles in the measurement sample but also classifying and counting the urinary particles.

In the present embodiment, detection of the urinary particles is preferably conducted by preparing a scattergram having two axes of scattered light information and fluorescence information, and analyzing the obtained scattergram by using appropriate analysis software. For example, when a scattergram is prepared having a fluorescent intensity on the X-axis and a forward scattered light intensity on the Y-axis, respective groups (clusters) appear on the scattergram in accordance with the particle size and the stainability (nucleic acid content) of the respective urinary particles. In the method of the present embodiment, at least casts and erythrocytes can be detected as two groups appearing in different areas. An analysis software provides windows which enclose the respective groups on the scattergram and allows count the number of particles in each window.

[Reagent for Analysis of Urine Sample]

Figure 6:
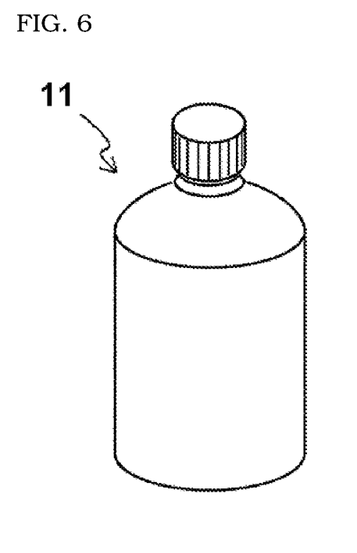
FIG. 6 shows one example of a reagent for analysis of urine sample.

A reagent for analysis of urine sample of the present embodiment (hereinafter, simply referred to as "reagent") is a reagent for detecting at least casts and erythrocytes as particles in a urine sample. The reagent of the present embodiment contains a surfactant at a concentration of more than or equal to 4 mg/L and less than or equal to 50 mg/L. The reagent of the present embodiment is a reagent that is to be mixed with a urine sample in such a manner that a concentration (final concentration) of the surfactant in the measurement sample prepared by mixing the urine sample and the reagent is more than or equal to to 2 mg/L and less than or equal to 30 mg/L, preferably more than or equal to 4 mg/L and less than or equal to 22 mg/L. The details of the reagent of the present embodiment are the same as those described for the first reagent used in the method for analyzing urine sample of the present embodiment. FIG. 6 shows one example of a reagent 11 of the present embodiment.

The scope of the present invention also encompasses use of a reagent containing more than or equal to 4 mg/L and less than or equal to 50 mg/L of a surfactant, for detecting at least casts and erythrocytes as particles in a urine sample.

[Reagent Kit for Analysis of Urine Sample]

A reagent kit for analysis of urine sample of the present embodiment (hereinafter, simply referred to as "reagent kit") is a reagent kit for detecting at least casts and erythrocytes as particles in a urine sample. The reagent kit of the present embodiment comprises a first reagent containing more than or equal to 4 mg/L and less than or equal to 50 mg/L of a surfactant, and a second reagent containing a fluorescent dye for staining casts and erythrocytes. The reagent kit of the present embodiment is a reagent kit to be mixed with a urine sample in such a manner that a concentration (final concentration) of the surfactant in the measurement sample prepared by mixing the urine sample, the first reagent and the second reagent is more than or equal to 2 mg/L and less than or equal to 30 mg/L, preferably more than or equal to 4 mg/L and less than or equal to 22 mg/L.

The details of the first reagent and the second reagent included in the reagent kit of the present embodiment are the same as those described for the first reagent and the second reagent used in the method for analyzing urine sample of the present embodiment.

Figure 7:
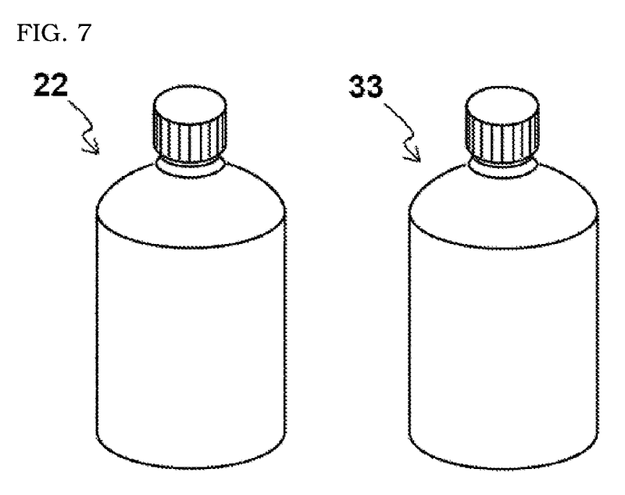
FIG. 7 shows one example of a reagent kit for analysis of urine sample.

In the present embodiment, it is preferable to store the first reagent and the second reagent in separate containers so as to provide a two-reagent type reagent kit comprising these reagents. FIG. 7 shows one example of a reagent kit of the present embodiment including a first reagent 22 stored in a container, and a second reagent 33 stored in a container.

The scope of the present invention also encompasses use of a reagent kit comprising a first reagent containing more than or equal to 4 mg/L and less than or equal to 50 mg/L of a surfactant, and a second reagent containing a fluorescent dye for staining casts and erythrocytes, for detecting at least casts and erythrocytes as particles in a urine sample.

The present invention is further described in detail hereinafter by way of examples which do not limit the present invention.

EXAMPLES

Example 1

In Example 1, the relationship between the concentration of the surfactant in the measurement sample prepared from a urine sample and the influence on the urinary erythrocytes was examined.

(1) Urine Sample

The urine sample used was a clinical sample for which erythrocytes were observed by a urinary sediment assay.

(2) Reagent

Diluting Reagent

As diluting agents, diluents 1 and 2 having the following compositions were prepared. For the diluents 1 and 2, water filtrated through a reverse osmosis membrane was used as a solvent.

Diluent 1: HEPES-OH (100 mM, pH7) (Dojindo Molecular Technologies, Inc.), EDTA-2K (25 mM) (Chubu Chelest Co., Ltd.) and DTAB (50 mg/L) (Tokyo Chemical Industry Co., Ltd.)

Diluent 2: HEPES-OH (100 mM, pH7), EDTA-2K (25 mM) and DTAB (10 mg/L)

Staining Reagent

The staining reagent was prepared by dissolving DioC3(3) (HAYASHIBARA CO., LTD.) which is a cyanine-based fluorescent dye in ethylene glycol (NACALAI TESQUE, INC.) to a concentration of 1 mg/mL.

(3) Measurement and Result

The samples were measured by using a flow cytometer UF-1000i (Sysmex Corporation). Specific steps of measurement by this flow cytometer are as follows. First, the urine sample (200 µL), the diluting reagent (580 µL) and the staining reagent (20 µL) were mixed and allowed to react at 40° C. for 10 seconds to prepare the measurement samples. The concentration of DTAB in the measurement samples (DTAB final concentration) was 36.25 mg/L when the diluent 1 was used and 7.25 mg/L when the diluent 2 was used. Then the measurement samples were irradiated with light, and the forward scattered light intensity and the fluorescence intensity were obtained. The flow cytometer had a light source of a semiconductor laser having an excitation wavelength of 488 nm. Based on these measurement values, the number of erythrocytes in the measurement samples was counted. The result is shown in FIG. 1 as the percentage (%) of the number of erythrocytes in the measurement samples to the number of erythrocytes contained in the urine sample that is not treated with a reagent.

Figure 1:
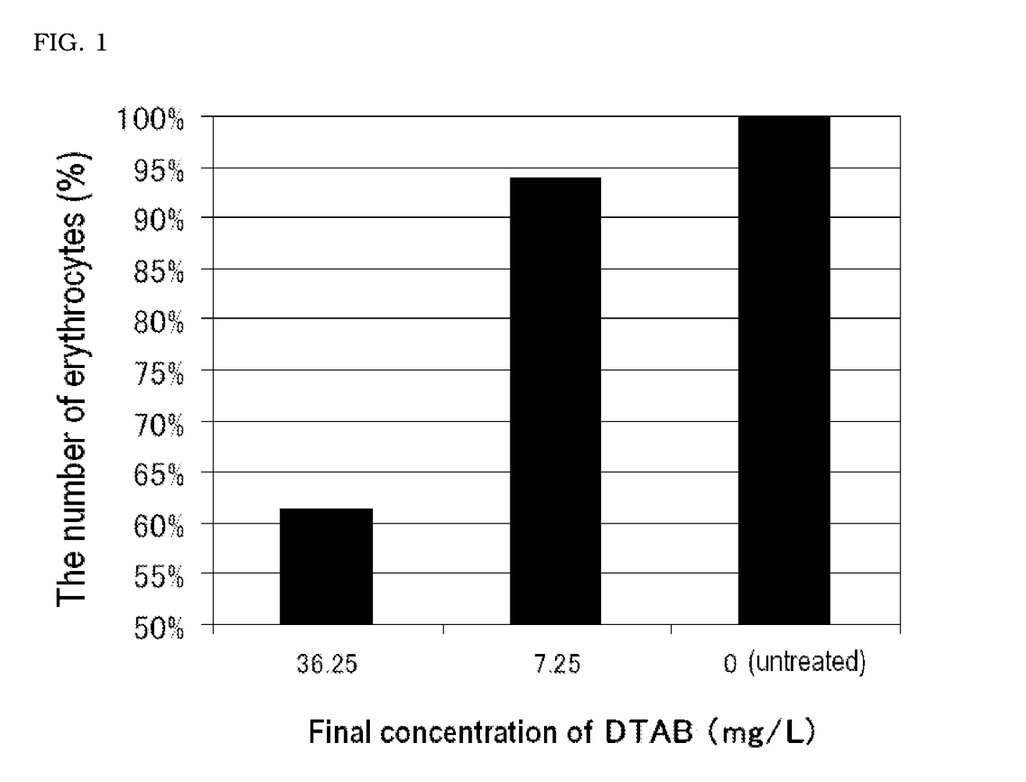
FIG. 1 shows a graph showing the number of erythrocytes contained in a measurement sample obtained by treating a urine sample containing the erythrocytes in the presence of a variable concentration of a surfactant.

As shown in FIG. 1, when the diluent 1 was used so that the final concentration of DTAB in the measurement sample was 36.25 mg/L, the number of erythrocytes in the measurement sample significantly decreased. Therefore, it is difficult to accurately count the erythrocytes in the urine sample in the condition that the final concentration of DTAB is 36.25 mg/L. In contrast, when the diluent 2 was used so that the final concentration of DTAB in the measurement sample was 7.25 mg/L, the influence on erythrocytes was very small. This reveals that the condition that the final concentration of DTAB is 7.25 mg/L is suitable for measurement of erythrocytes in the urine sample.

Example 2

In Example 2, the performance of discriminating mucus threads which are urinary particles having a resemblance to casts, from casts by the method for analyzing urine sample of the present embodiment using a flow cytometer was examined.

(1) Urine Sample

The urine samples used were urine containing mucus threads (clinical sample in which mucus threads were observed in a urinary sediment assay, hereinafter also referred to as "false positive sample") and urine containing casts and mucus threads (clinical sample in which casts and mucus threads were observed by the urinary sediment assay, hereinafter also referred to as "cast sample").

(2) Reagent

Diluting Reagent

As diluting reagents, diluents 3 and 4 having the following compositions were prepared. For the diluents 3 and 4, water filtrated through a reverse osmosis membrane was used as a solvent.

Diluent 3: HEPES-OH (100 mM, pH7) and EDTA-2K (25 mM)

Diluent 4: HEPES-OH (100 mM, pH7), EDTA-2K (25 mM) and DTAB (10 mg/L)

Staining Reagent

As a staining reagent, the same staining reagent as in Example 1 was used.

(3) Measurement and Result

The urine sample (200 µL), the diluting reagent (580 µL) and the staining reagent (20 µL) were mixed and allowed to react at 40° C. for 10 seconds to prepare the measurement samples. Then the obtained measurement samples were visually observed under a fluorescence microscope BX51 (Olympus Corporation) to count the casts. Also, measurement samples were prepared in the same manner, and the obtained measurement samples were measured also by a flow cytometer UF-1000i (Sysmex Corporation). Specifically, the measurement samples were irradiated with light, and the forward scattered light intensity, the side scattered light intensity and the fluorescence intensity were obtained. The flow cytometer had a light source of a semiconductor laser having an excitation wavelength of 488 nm. Based on these measurement values, the number of casts in the measurement samples was calculated. The result is shown in Table 1. The result of the visual observation under the fluorescence microscope is the number of casts in the sample treated with the diluent 3.

TABLE 1

| | Number of casts (particles/µL) | | |
|---|---|---|---|
| | Visual observation | FCM, Diluent 3 (DTAB final concentration 0 mg/L) | FCM, Diluent 4 (DTAB final concentration 7.25 mg/L) |
| False positive sample | 0.4 | 2.8 | 0.5 |
| Cast sample | 10 | 14.5 | 9.4 |

As shown in Table 1, in the urine samples treated with the diluent 3 not containing DTAB, the calculated number of casts based on the measurement by the flow cytometer (FCM) was larger than the number counted by the visual observation. This is attributable to the fact that the impurities which resemble casts, such as aggregates of mucus threads in the sample were counted as casts. On the other hand, in the urine sample treated with the diluent 4 containing DTAB, it was revealed that the measurement result of FCM approximates to the result of the visual observation. This is attributable to the fact that the impurities which resemble casts were reduced by the action of DTAB.

Example 3

In Example 3, the clinical performance of the method for analyzing urine sample using a flow cytometer according to the present embodiment was evaluated in comparison with the result of the visual observation.

(1) Urine Sample

The urine samples used were negative urine samples (42 samples) in which appearance of casts were not observed by observation under a microscope.

(2) Reagent

As the diluting reagents, the diluents 3 and 4 that are the same as those in Example 2 were used. As a staining reagent, the same staining reagent as in Example 1 was used.

(3) Measurement and Result

The samples were measured by using a flow cytometer UF-1000i (Sysmex Corporation). Specific steps of measurement by this flow cytometer are as follows. First, the sample (200 µL), the diluting reagent (580 µL) and the staining reagent (20 µL) were mixed and allowed to react at 40° C. for 10 seconds to prepare the measurement samples. Then the obtained measurement samples were irradiated with light, and the forward scattered light intensity, the side scattered light intensity and the fluorescence intensity were obtained. The flow cytometer had a light source of a semiconductor laser having an excitation wavelength of 488 nm. Based on these measurement values, the number of casts in the measurement samples was calculated, and the number of the samples that were decided as negative by the flow cytometer (FCM) was determined. Also the specificity of the analysis of casts by the FCM was determined by referring to the number of negative samples by the visual observation (microscopic observation). The result is shown in Table 2.

TABLE 2

|  | Diluent 3 (DTAB final concentration 0 mg/L) | Diluent 4 (DTAB final concentration 7.25 mg/L) |
| --- | --- | --- |
| Number of negative samples by visual observation | 42 | 42 |
| Number of negative samples by FCM | 30 | 36 |
| Specificity (%) | 71.4 | 85.7 |

As shown in Table 2, when the urine samples were treated with the staining reagent containing a cyanine-based fluorescent dye and the diluent not containing a dispersant, the specificity of the analysis by the FCM measurement was 71.4%. In contrast, when the urine samples were treated with the diluent containing DTAB which is a cationic surfactant as a dispersant, the specificity of the analysis was improved. This is attributable to the fact that the impurities which resemble casts were reduced by the action of DTAB.

Example 4

In Example 4, the relationship between the concentration of the surfactant in the measurement sample prepared from a urine sample and the influence on the urinary erythrocytes was examined.

(1) Urine Sample

The urine sample used was the clinical sample for which erythrocytes were observed by the urinary sediment assay.

(2) Reagent

Diluting Reagent

As diluting reagents, a series of diluents containing various surfactants in various concentrations were prepared. The compositions are as follows. For each diluent, water filtrated through a reverse osmosis membrane was used as a solvent.

(i) A series of diluents containing one kind of the following cationic surfactants: HEPES-OH (50 mM, pH7) (Dojindo Molecular Technologies, Inc.), EDTA-2K (25 mM) (Chubu Chelest Co., Ltd.) and a cationic surfactant (0, 5, 10, 15, 20 or 30 mg/L)

Cationic Surfactants

Octyltrimethylammonium bromide (OTAB) (TOKYO CHEMICAL INDUSTRY CO., LTD.)

Dodecyltrimethylammonium bromide (DTAB) (TOKYO CHEMICAL INDUSTRY CO., LTD.)

Tetradecyltrimethylammonium bromide (MTAB) (TOKYO CHEMICAL INDUSTRY CO., LTD.)

Dodecyltrimethylammonium chloride (DTAC) (TOKYO CHEMICAL INDUSTRY CO., LTD.)

(ii) A series of diluents containing one kind of the following nonionic surfactants: HEPES-OH (50 mM, pH7), EDTA-2K (25 mM) and a nonionic surfactant (0, 5, 10, 15, 20 or 30 mg/L)

Nonionic Surfactants

Polyoxyethylene cetylether (BC-7 (Nikko Chemicals Co., Ltd.))

Staining Reagent

The staining reagent was prepared by dissolving DiOC3(3) (HAYASHIBARA CO., LTD.) which is a cyanine-based fluorescent dye in ethylene glycol (NACALAI TESQUE, INC.) to a concentration of 1 mg/mL.

(3) Measurement and Result (3-1) Diluent Containing One Kind of Cationic Surfactant The samples were measured by using a flow cytometer UF-1000i (Sysmex Corporation). Specific steps of measurement by this flow cytometer are as follows. First, the urine sample (200 μL), the diluting reagent (580 μL) and the staining reagent (20 μL) were mixed and allowed to react at 40° C. for 10 seconds to prepare the measurement samples. The concentrations of the surfactant in the measurement samples (final concentration) were 0, 3.6, 7.3, 10.9, 14.5 and 21.8 mg/L. Then the measurement samples were irradiated with light, and a forward scattered light intensity and a fluorescence intensity were obtained. The flow cytometer had a light source of a semiconductor laser having an excitation wavelength of 488 nm. Based on these measurement values, the number of erythrocytes in the measurement samples was counted. The result is shown in FIG. 2.

(3-2) Diluent Containing One Kind of Nonionic Surfactant

Figure 3:
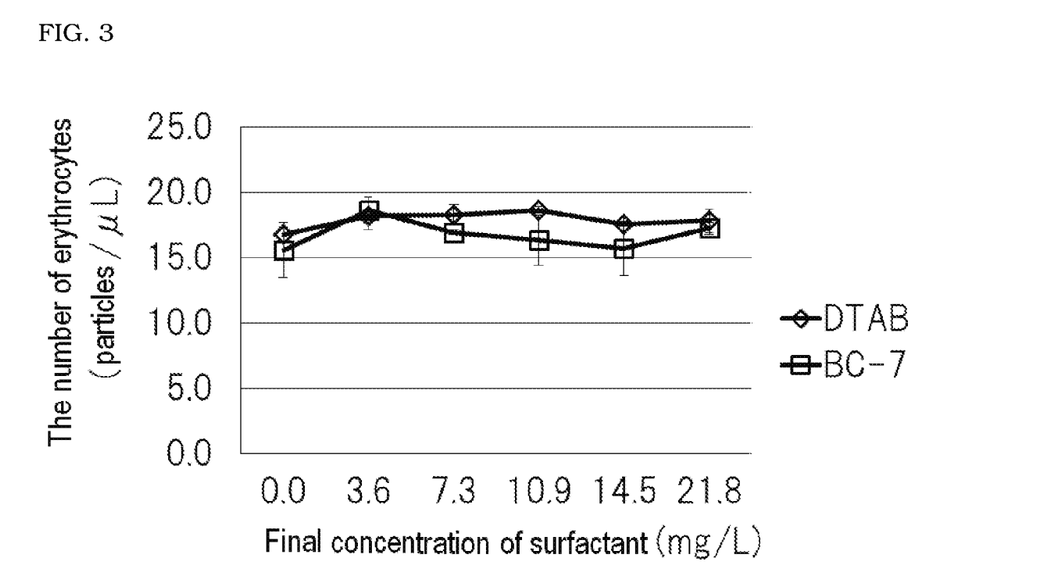
FIG. 3 shows a graph showing the number of erythrocytes detected from a measurement sample obtained by treating a urine sample containing the erythrocytes in the presence of a variable concentration of a nonionic surfactant or a cationic surfactant.

Measurement samples were prepared in the same manner as described above except that the series of diluents containing BC-7 was used as the diluting reagent. The concentrations of the surfactant in the measurement samples (final concentration) were 0, 3.6, 7.3, 10.9, 14.5 and 21.8 mg/L. These samples were measured in the same manner as described in the above. For comparison, the measurement samples were measured in the same manner by using the series of diluents containing DTAB. Then based on the obtained measurement values, the number of erythrocytes in the measurement samples was counted. The result is shown in FIG. 3.

Figure 2:
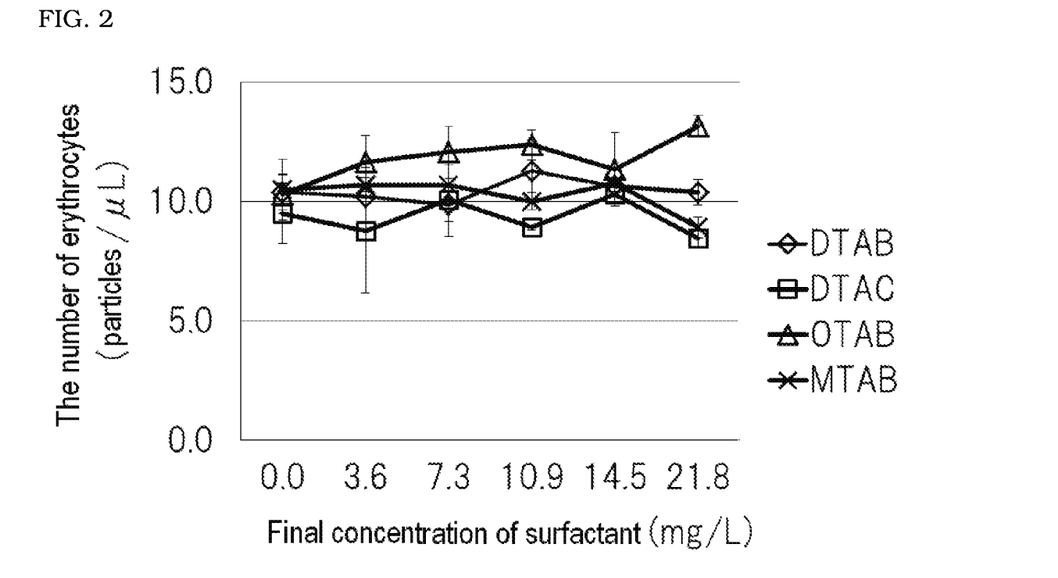
FIG. 2 shows a graph showing the number of erythrocytes detected from a measurement sample obtained by treating a urine sample containing the erythrocytes in the presence of a variable concentration of a cationic surfactant.

As shown in FIG. 2, it is found that the number of erythrocytes in the measurement sample does not decrease and can be measured accurately even when a cationic surfactant other than DTAB is used. As shown in FIG. 3, it is found that the number of erythrocytes in the measurement sample does not decrease and can be measured accurately likewise the case of using DTAB even when a nonionic surfactant is used.

Example 5

In Example 5, the relationship between the concentration of the surfactant in the measurement sample prepared from a urine sample and the effect of reducing impurities which resemble casts was examined.

(1) Urine Sample

The urine sample used was the normal sample not containing casts but containing impurities which resemble casts.

(2) Reagent

Diluting reagent

As a diluting reagent, a series of diluents containing various surfactants in various concentrations were prepared. The compositions are as follows. For each diluent, water filtrated through a reverse osmosis membrane was used as a solvent.

(iii) A series of diluents containing one kind of the following cationic surfactants: HEPES-OH (50 mM, pH7) (Dojindo Molecular Technologies, Inc.), EDTA-2K (25 mM) (Chubu Chelest Co., Ltd.) and a cationic surfactant (0, 1, 3, 5, 8, 10, 20 or 50 mg/L)

Cationic Surfactants

Octyltrimethylammonium bromide (OTAB) (TOKYO CHEMICAL INDUSTRY CO., LTD.)

Dodecyltrimethylammonium bromide (DTAB) (TOKYO CHEMICAL INDUSTRY CO., LTD.)

Tetradecyltrimethylammonium bromide (MTAB) (TOKYO CHEMICAL INDUSTRY CO., LTD.)

Dodecyltrimethylammonium chloride (DTAC) (TOKYO CHEMICAL INDUSTRY CO., LTD.)

(iv) A series of diluents containing one kind of the following nonionic surfactants: HEPES-OH (50 mM, pH7), EDTA-2K (25 mM), and a nonionic surfactant (0, 1, 3, 5, 8, 10, 20 or 50 mg/L)

Nonionic Surfactants

Polyoxyethylene cetylether (BC-7 (Nikko Chemicals Co., Ltd.))

Staining Reagent

As the staining reagent, the same staining reagent as in Example 4 was used.

(3) Measurement and Result (3-1) Diluent Containing One Kind of Cationic Surfactant The samples were measured by using a flow cytometer UF-1000i (Sysmex Corporation). Specific steps of measurement by this flow cytometer are as follows. First, the urine sample (200 μL), the diluting reagent (580 μL) and the staining reagent (20 μL) were mixed and allowed to react at 40° C. for 10 seconds to prepare the measurement samples. The concentrations of the surfactant in the measurement samples (final concentration) were 0, 0.7, 2.2, 3.6, 5.8, 7.3, 14.5 and 36.3 mg/L. Then the measurement samples were irradiated with light, and the forward scattered light intensity and the fluorescence intensity were obtained. The flow cytometer had a light source of a semiconductor laser having an excitation wavelength of 488 nm. Based on these measurement values, the number of impurities which resemble casts in the measurement samples was counted. The result is shown in FIG. 4.

(3-2) Diluent Containing One Kind of Nonionic Surfactant

Figure 5:
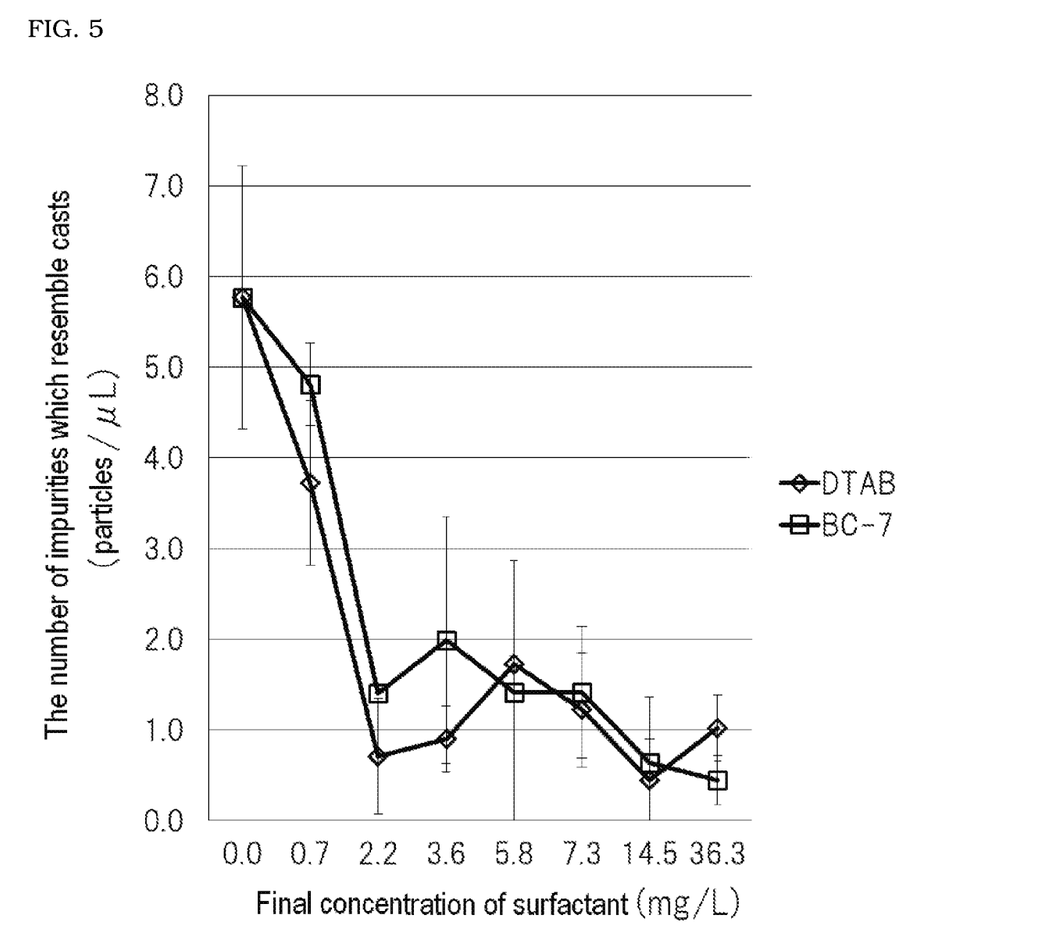
FIG. 5 shows a graph showing the number of impurities detected from a measurement sample obtained by treating a urine sample not containing the casts but containing the impurities which resemble the casts in the presence of a variable concentration of a nonionic surfactant or a cationic surfactant.

Measurement samples were prepared in the same manner as described above except that the series of diluents containing BC-7 was used as the diluting reagent. The concentrations of the surfactant in the measurement samples (final concentration) were 0, 0.7, 2.2, 3.6, 5.8, 7.3, 14.5 and 36.3 mg/L. These samples were measured in the same manner as described in the above. For comparison, the measurement samples were measured in the same manner by using the series of diluents containing DTAB. Then based on the obtained measurement values, the number of impurities which resemble casts in the measurement sample was counted. The result is shown in FIG. 5.

Figure 4:
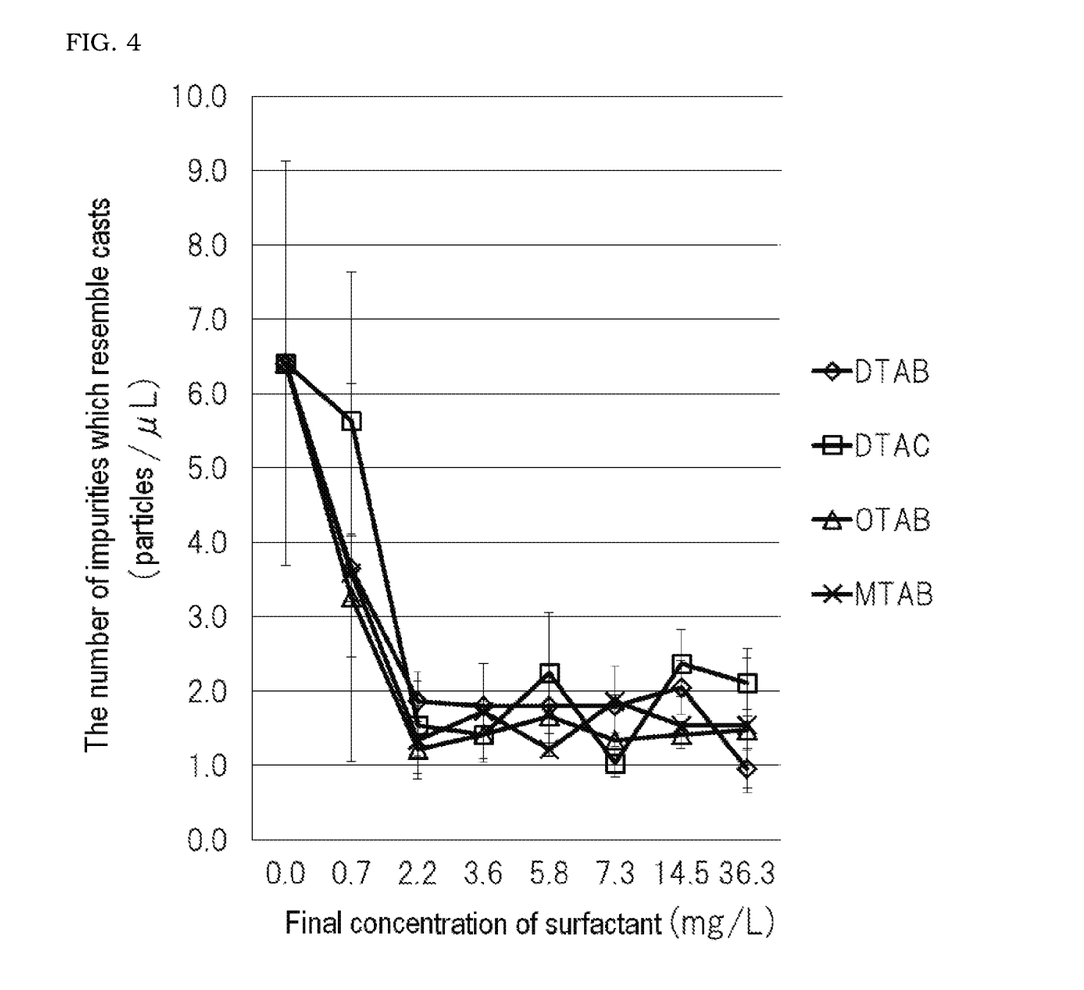
FIG. 4 shows a graph showing the number of impurities detected from a measurement sample obtained by treating a urine sample not containing the casts but containing the impurities which resemble the casts in the presence of a variable concentration of a cationic surfactant.

As shown in FIG. 4, when the concentration of the cationic surfactant in the measurement sample was more than or equal to 2.2 mg/L, the number of detected impurities decreased in comparison with the cases of 0 and 0.7 mg/L. As shown in FIG. 5, also in the case where the nonionic surfactant BC-7 was used, the number of detected impurities decreased likewise the case of using DTAB when the concentration of the surfactant was more than or equal to 2.2 mg/L. These results reveal that by setting the concentration of the surfactant in the measurement sample at more than or equal to 2.2 mg/L, it is possible to reduce the impurities that would otherwise be detected erroneously as casts.

The present application relates to Japanese patent application No. 2014-039282 filed on Feb. 28, 2014, and the entirety of claims, description and abstract are incorporated into the present specification by reference.

REFERENCE SIGNS LIST

11: Reagent for analysis of urine sample
22: First reagent
33: Second reagent

What is claimed is:

1. A method for analyzing a urine sample, comprising the steps of:
preparing a measurement sample by mixing the urine sample, a surfactant selected from the group consisting of a cationic surfactant and a nonionic surfactant, and a fluorescent dye capable of staining casts and erythrocytes; and
detecting at least casts and erythrocytes as urinary particles contained in the measurement sample obtained from the preparation step,
wherein a concentration of the surfactant in the measurement sample obtained from the preparation step is more than or equal to 2 mg/L and less than or equal to 30 mg/L,
wherein when the concentration of the surfactant is more than or equal to 2 mg/L, a number of impurities which resemble the casts is decreased as compared to a case where the concentration of the surfactant is less than 2 mg/L, and
wherein when the concentration of the surfactant is less than or equal to 30 mg/L, a number of the erythrocytes is increased as compared to a case where the concentration of the surfactant is greater than 30 mg/L.

2. The method for analyzing the urine sample according to claim 1, wherein the concentration of the surfactant in the measurement sample obtained from the preparation step is more than or equal to 4 mg/L and less than or equal to 22 mg/L.

3. The method for analyzing the urine sample according to claim 1, wherein the cationic surfactant is at least one selected from a quaternary ammonium salt type surfactant and a pyridinium salt type surfactant.

4. The method for analyzing the urine sample according to claim 3, wherein the cationic surfactant is the quaternary ammonium salt type surfactant.

5. The method for analyzing the urine sample according to claim 4, wherein the quaternary ammonium salt type surfactant is a surfactant having 4 to 38 carbon atoms in total represented by the following formula (I):

wherein $R_1$ is an alkyl or alkenyl group having 1 to 18 carbon atoms; $R_2$ and $R_3$ are the same or different from each other and are respectively an alkyl or alkenyl group having 1 to 4 carbon atoms; $R_4$ is an alkyl or alkenyl group having 1 to 12 carbon atoms, or a benzyl group; and $X^-$ is a halogen ion or a hydroxyl ion.

6. The method for analyzing the urine sample according to claim 4, wherein the quaternary ammonium salt type surfactant is at least one selected from dodecyltrimethylammonium bromide, octyltrimethylammonium bromide, tetradecyltrimethylammonium bromide, dodecyltrimethylammonium chloride, octyltrimethylammonium chloride and tetradecyltrimethylammonium chloride.

7. The method for analyzing the urine sample according to claim 5, wherein each of $R_2$, $R_3$ and $R_4$ defined in the formula (I) is a methyl group.

8. The method for analyzing the urine sample according to claim 5, wherein $X^-$ defined in the formula (I) is the halogen ion and at least one selected from a bromide ion, a chloride ion and an iodide ion.

9. The method for analyzing the urine sample according to claim 1, wherein the fluorescent dye for staining the casts and the erythrocytes is a cyanine-based fluorescent dye.

10. The method for analyzing the urine sample according to claim 1, wherein the method further comprises a step of obtaining optical information by irradiating the urinary particles contained in the measurement sample with light,
wherein the detection step is a step of detecting at least the casts and the erythrocytes as the urinary particles, based on the obtained optical information.

11. The method for analyzing the urine sample according to claim 10, wherein the optical information comprises at least scattered light information.

12. The method for analyzing the urine sample according to claim 1, wherein the measurement sample containing the surfactant further comprises a chelating agent.

13. The method for analyzing the urine sample according to claim 12, wherein the chelating agent is ethylenediaminetetraacetate (EDTA) salt.

14. The method for analyzing the urine sample according to claim 1, wherein the surfactant is selected from the group consisting of dodecyltrimethylammonium bromide, dodecyltrimethylammonium chloride, octyltrimethylammonium bromide, polyoxyethylene cetylether, and tetradecyltrimethylammonium bromide.

15. The method for analyzing the urine sample according to claim 14, wherein the surfactant is dodecyltrimethylammonium bromide.

16. The method for analyzing the urine sample according to claim 14, wherein the concentration of the surfactant in the measurement sample obtained from the preparation step is 7.25 mg/L.

17. The method for analyzing the urine sample according to claim 15, wherein the concentration of the surfactant in the measurement sample obtained from the preparation step is 7.25 mg/L.

18. The method for analyzing the urine sample according to claim 1, wherein the nonionic surfactant is a polyoxyethylene-based nonionic surfactant.

19. The method for analyzing the urine sample according to claim 18, wherein the polyoxyethylene-based nonionic surfactant is polyoxyethylene alkyl ether.

* * * * *